March 20, 1951 H. C. SWIM Plant Pat. 1,008
BERRY PLANT
Filed Feb. 7, 1950
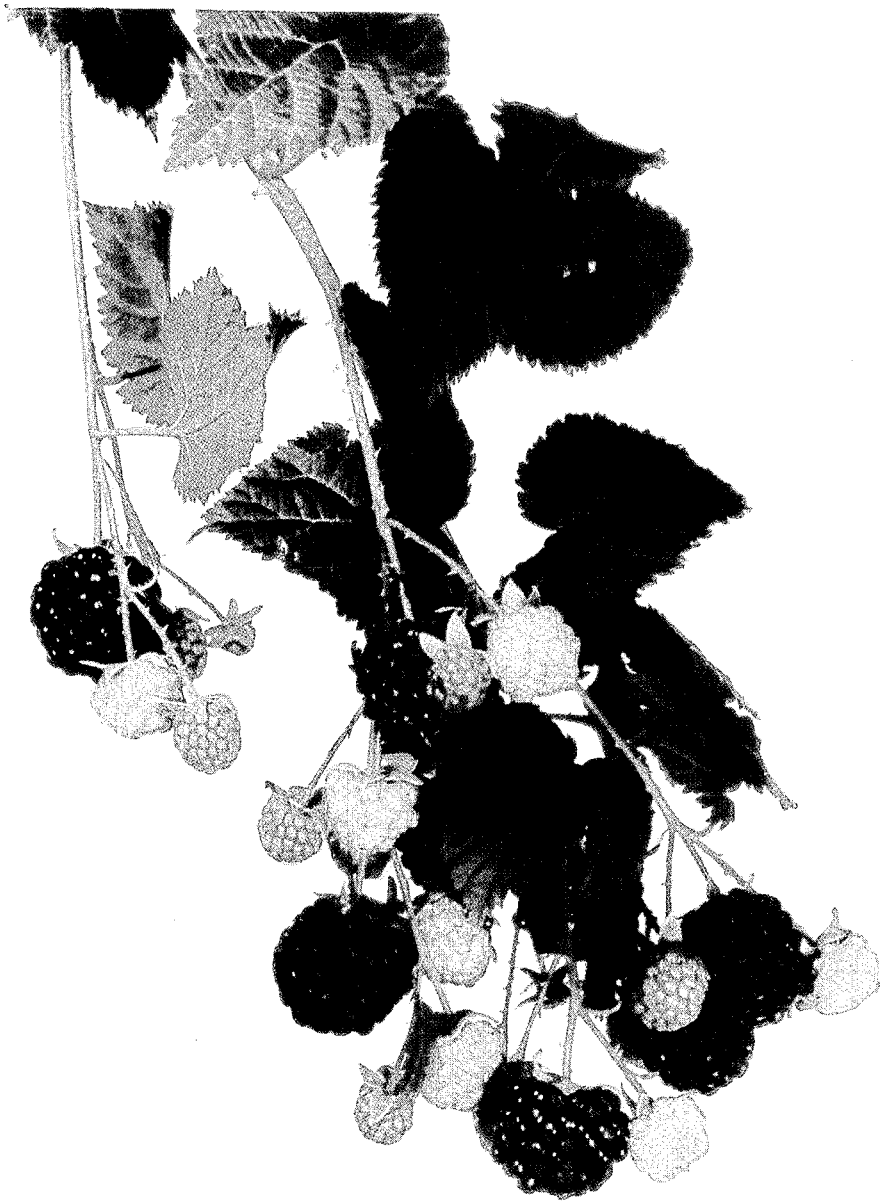
Inventor.
H. C. Swim
By: Robbs & Cobb
Attorneys.

Patented Mar. 20, 1951

Plant Pat. 1,008

UNITED STATES PATENT OFFICE 1,008

BERRY PLANT

Herbert C. Swim, Ontario, Calif., assignor to Armstrong Nurseries, Inc., Ontario, Calif., a corporation of California Application February 7, 1950, Serial No. 142,779

1 Claim. (Cl. 47—62)

The present invention or discovery relates to a new and distinct variety of berry plant which is the result of a cross pollenation of "Nessberry" with "Sodus Purple" raspberry and continuing to the third filial generation.

This new variety has a number of very important distinctive characteristics such as very great vigor of the plant which produces long and strong canes clothed with medium to large, heavy, semi-glossy leaves that have a somewhat rugose character, and with a marked resistance to such diseases as mildew, cane blight and anthracnose.

The fruit size is extraordinarily large and comparable to the boysenberry, but with much greater productivity measured principally by the number of fruit per cluster, which is seldom greater than seven in the boysenberry, but which is seldom less than seven, and as many as thirty or more in this new variety. The fruit is borne in large clusters which hang down over almost the entire surface of the plant.

Another important characteristic of the fruit is that the flavor of both the red raspberry and blackberry varieties of the background parentage are apparent. The fruit is nearly round in shape and of distinctive color as described and illustrated herein, with soft seeds which are unnoticeable when the berries are eaten.

In comparison with its parent, which is a second filial generation seedling from the cross of "Nessberry" by "Sodus Purple" raspberry, the fruit of the new variety is more readily separated from the stem in picking, the flavor is a better blend between the two types of berries used in the original cross, is sweeter to the taste than the fruit of the mother plant, and is more glossy as the result of fewer and shorter hairs on the drupelets.

Plants of this new variety are in habit and appearance more like those of the blackberry type, and the berries may be picked more readily with the receptacle or core remaining in the fruit, although they can also be picked with the receptacle or core remaining attached to the stems of the plants.

Asexual reproduction by runners at Ontario, California, proves that these characteristics are fixed and established, and hold through succeeding propagations.

In the drawing, the figure illustrates specimens of the canes, foliage and berries, the latter being in different stages of maturity.

The following description specifically sets forth the characteristics of this new variety of berry, with all color references according to Ridgway's Color Standards and Nomenclature. Observations were made at Ontario, California.

Dates of first and last picking are somewhat variable with the seasons, but principally are from June 15th to July 15th, or slightly later.

Plant: Large; vigorous; trailing; dense; tall; hardy as to heat; very productive; regular bearer; deciduous.

Propagation: Holds its distinguishing characteristics through succeeding propagations.

Environment: Sun.

Canes: Tall; trailing; rough; prickly; stout. Mature color—near Lime Green, Plate XXXI.

Prickles:

*Large prickles.*—Many; medium length; hooked downward slightly; with short, narrow base. Color—Walnut Brown, Plate XXVIII, at dried tip, often with an area of Acajou Red, Plate XIII, near the base before it shades into the Lime Green, Plate XXXI, of the cane.

*Small prickles.*—Color—Walnut Brown, Plate XXVIII, at dried tip, often with an area of Acajou Red, Plate XIII, near the base before it shades into the Lime Green, Plate XXXI, of the cane.

*Hairs.*—None.

New shoots: Color—near Lettuce Green, Plate V.

*Large prickles.*—Many; medium length; hooked slightly downward; with short, narrow base. Color — tips are Calliste Green, Plate VI, shading toward the base to Cosse Green, Plate V, many prickles tinted with Acajou Red, Plate XIII, near the base.

*Small prickles.*—Several. Color—most with Calliste Green, Plate VI, some tinted in the basal region with Acajou Red, Plate XIII, some small prickles especially near and at the base of the Rachis, entirely or nearly all Acajou Red, Plate XIII.

*Hairs.*—None.

*Tomentum.*—None.

*Bloom.*—None.

Foliage:

*Leaves.*—Compound of usually three but often five leaflets.

*Leaflets.*—Abundant; medium to large; heavy; semi-glossy; somewhat rugose. Shape—cordate with apex acuminate; base cordate; margin doubly serrate. Color—mature—upper surface: near Cedar Green, Plate VI; under surface: between Calla Green, Plate V, and Light Elm Green, Plate XVII. Measurements—8.5 cm. average length from base to apex, and 5.5 cm. average breadth at widest point. Variations—some leaflets are ovate in form with round base instead of the cordate base. Color—young—upper surface: between Forest Green, Plate XVII, and Bice Green, Plate XVII; under surface: near Biscay Green, Plate XVII. Variations—upper surface of newly opened leaves appear oily, leaf color lightest at early stages of ontogeny. Young foliage lightly pubescent on under surface especially along veins and midrib. This light pubescence is less on more mature leaflets. Small stipules are also present on midrib of the leaflets, most numerous on immature leaflets. These stipules recurve toward the point of leaflet attachment.

*Rachis.*—Heavy. Upper side—grooved slightly, and most prominently near the point of attachment; under side—moderately prickly.

*Stipules.*—Stipule base adnate for short distance up the adaxial surface of the rachis. Points of the stipule are long and very narrow turning slightly outward.

*Flowers borne.*—Several to stem; 7 to 35 in irregular cluster; on strong, medium length cymes; axillary; perfect; complete.

*Quantity of bloom.*—Abundant.

*Continuity.*—One season.

Flower:

*Pedicel.*—Medium long, 1 to 3 cm.; medium to heavy caliper; rough; numerous prickles. Color—usually near Apple Green, Plate XVII.

*Before calyx breaks.*—Size—small. Form—globular with a pubescence on the surface of the bud.

*Calyx.*—Inner surface—with tomentum; margins also with tomentum; outer surface—with tomentum.

*Bloom.*—When fully open—large; 2 cm. to 2½ cm. Petalage—single; petals arranged regularly. Form—flat to cupped.

*Petals.*—Thin; soft; 1 cm. or less in length. Color—outside and inside surface—near white.

Reproductive organs:

*Stamens.*—Very many, approximately 120.

*Filaments.*—Medium length, approximately 5 mm.; near white in color; most with anthers.

*Anthers.*—Very small, ⅓ mm.

*Pollen.*—Moderate.

*Pistils.*—Many; approximately 120.

*Sepals.*—Persistent; moderately short, approximately 6 mm.; spear-shaped.

Fruit: Maturity when described, June 23th.

*Size of berry.*—Approximately the size of boysenberry; fairly uniform; large. Diameter—2.5 cm. Transverse base to apex—2.25 cm.

*Number of clusters.*—40 to 60.

*Number of berries to clusters.*—7 to 35.

*Shape.*—Nearly round.

*Form of drupelets.*—Uniform; symmetrical; obovoid more or less hexagonal in cross-section through broadest portion; large; compact; drupelets persist to receptacle somewhat.

*Sterility.*—All drupelets mature.

*Skin.*—Thin; medium tender.

*Tomentum.*—Bloom or hairs—moderate; short; does not rub off easily.

*Color of ripe berry.*—Near Aniline Black, Plate L.

*Ripening.*—Began June 7th; peak June 28th; end July 15th.

*Ripens.*—Evenly.

*Texture.*—Firm; melting.

*Flavor.*—Slightly acid.

*Aroma.*—Pronounced and distinct.

*Eating quality.*—Fair to good.

*Cooking quality.*—Excellent.

Seed:

*Size.*—Medium.

*Length.*—3 mm.

*Breadth.*—2 mm.

*Form.*—Obovoid; somewhat irregular in shape.

Use: Home; dessert; canning; excellent for jams and jellies.

Keeping quality: Good.

Shipping quality: Good. Berry holds its shape on picking; holds together after picking but picks with slight difficulty.

Disease: Resistant to pests; fungus; mildew; blight and anthracnose.

I claim:

A new and distinct variety of berry plant characterized as to novelty by the very great vigor of the plant, production of long and strong canes, clothed with medium to large, heavy, semi-glossy leaves of a somewhat rugose character, marked resistance to such diseases as mildew, cane blight and anthracnose, with large, nearly round, more glossy fruit comparable in size to the boysenberry but of much greater productivity as measured principally by the greater number of fruit per cluster, said fruit having a distinctive color and a sweeter and better blend of flavor combining that of the red raspberry and blackberry, and being distinguished from its parent by being more readily separated from the stem in picking, substantially as shown and described.

HERBERT C. SWIM.

No references cited.